(12) United States Patent
Leeflang et al.

(10) Patent No.: US 11,517,662 B2
(45) Date of Patent: *Dec. 6, 2022

(54) INJECTION DEVICES AND SYSTEMS AND METHODS FOR USING THEM

(71) Applicant: CLPH, LLC, Palo Alto, CA (US)

(72) Inventors: Stephen A. Leeflang, Sunnyvale, CA (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 16/707,775

(22) Filed: Dec. 9, 2019

(65) Prior Publication Data

US 2020/0215259 A1 Jul. 9, 2020

Related U.S. Application Data

(63) Continuation of application No. 15/284,466, filed on Oct. 3, 2016, now Pat. No. 10,500,332.

(Continued)

(51) Int. Cl.
*A61M 5/14* (2006.01)
*A61M 25/00* (2006.01)
*A61B 34/20* (2016.01)
*A61M 5/00* (2006.01)
*A61M 5/145* (2006.01)
(Continued)

(52) U.S. Cl.
CPC .......... *A61M 5/1407* (2013.01); *A61B 34/20* (2016.02); *A61M 5/007* (2013.01); *A61M 5/1452* (2013.01); *A61M 5/158* (2013.01); *A61M 25/005* (2013.01); *A61M 25/0026* (2013.01); *A61M 25/0084* (2013.01); *A61B 2090/3966* (2016.02); *A61M 5/14* (2013.01); *A61M 2005/2013* (2013.01); *A61M 2025/0089* (2013.01)

(58) Field of Classification Search
CPC .......... A61M 25/0009; A61M 25/0026; A61M 5/1407; A61M 5/007; A61M 5/1452; A61M 5/158; A61B 34/20
See application file for complete search history.

(56) References Cited

U.S. PATENT DOCUMENTS

| | | | | |
|---|---|---|---|---|
| 4,920,967 A | * | 5/1990 | Cottonaro | A61B 1/0056 600/465 |
| 5,964,740 A | * | 10/1999 | Ouchi | A61M 25/0084 604/164.01 |
| 10,500,332 B2 | * | 12/2019 | Leeflang | A61M 25/0026 |

* cited by examiner

*Primary Examiner* — Tasnim Mehjabin Ahmed
(74) *Attorney, Agent, or Firm* — William A. English; Vista IP Law Group LLP

(57) ABSTRACT

Systems and methods are provided for injecting one or more agents into tissue within a patient's body. In one embodiment, an injection device includes a substantially axially incompressible elongate member including a lumen extending between proximal and distal ends thereof. A distal stop is provided on the distal end and a needle tip extends distally beyond the distal stop, the needle tip having a cross-section smaller than the distal end. The needle tip includes a passage communicating between the lumen and an outlet in the distal tip that has having a cross-section smaller than the lumen. In an exemplary embodiment, the elongate member includes a coil extending between the proximal and distal ends, and a sleeve disposed within an interior region of the coil extending between the proximal and distal ends. The sleeve defines the lumen and may be free-floating within at least a portion of the coil.

20 Claims, 6 Drawing Sheets

Related U.S. Application Data

(60) Provisional application No. 62/299,553, filed on Feb. 24, 2016, provisional application No. 62/250,125, filed on Nov. 3, 2015.

(51) Int. Cl.
*A61M 5/158* (2006.01)
*A61B 90/00* (2016.01)
*A61M 5/20* (2006.01)

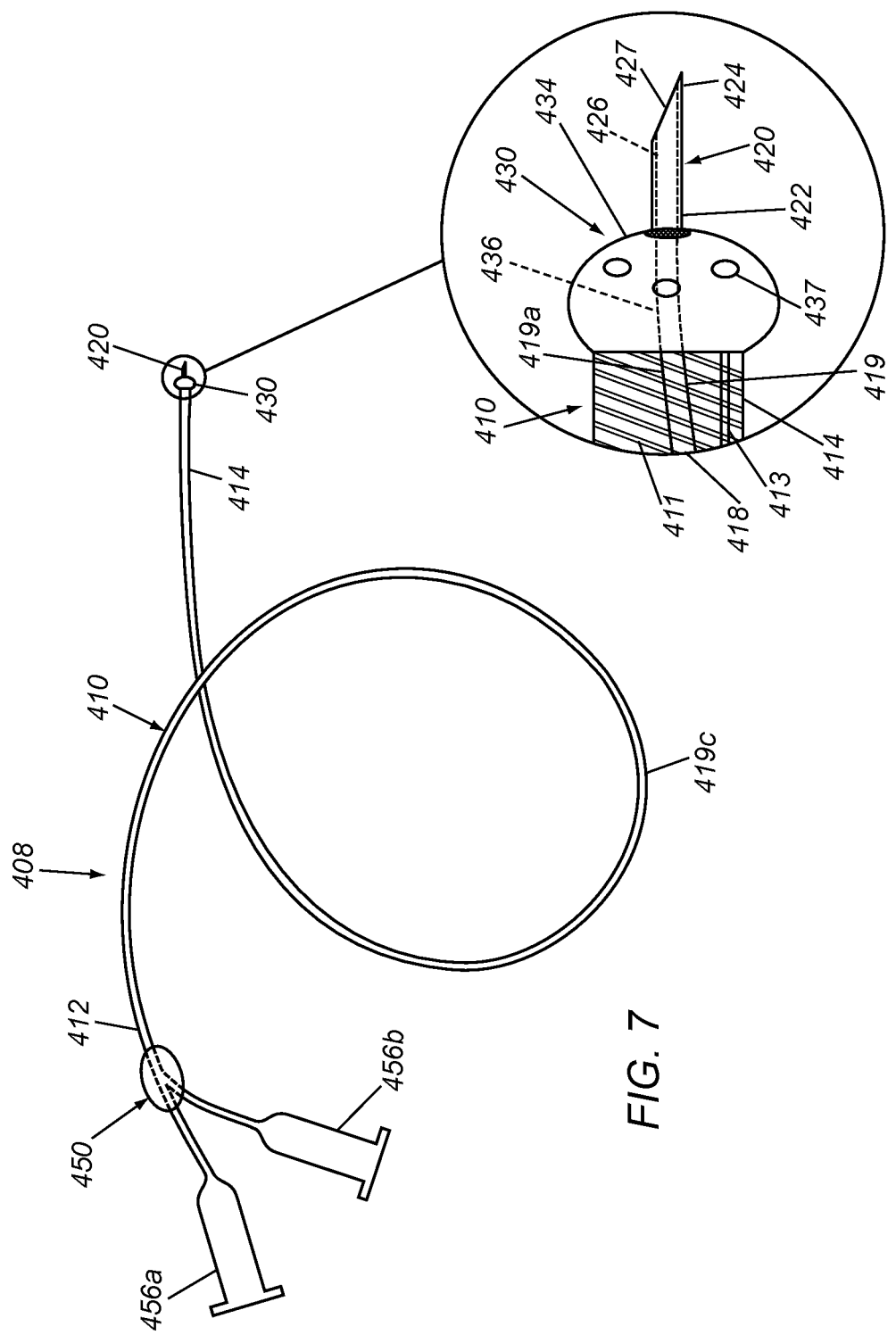

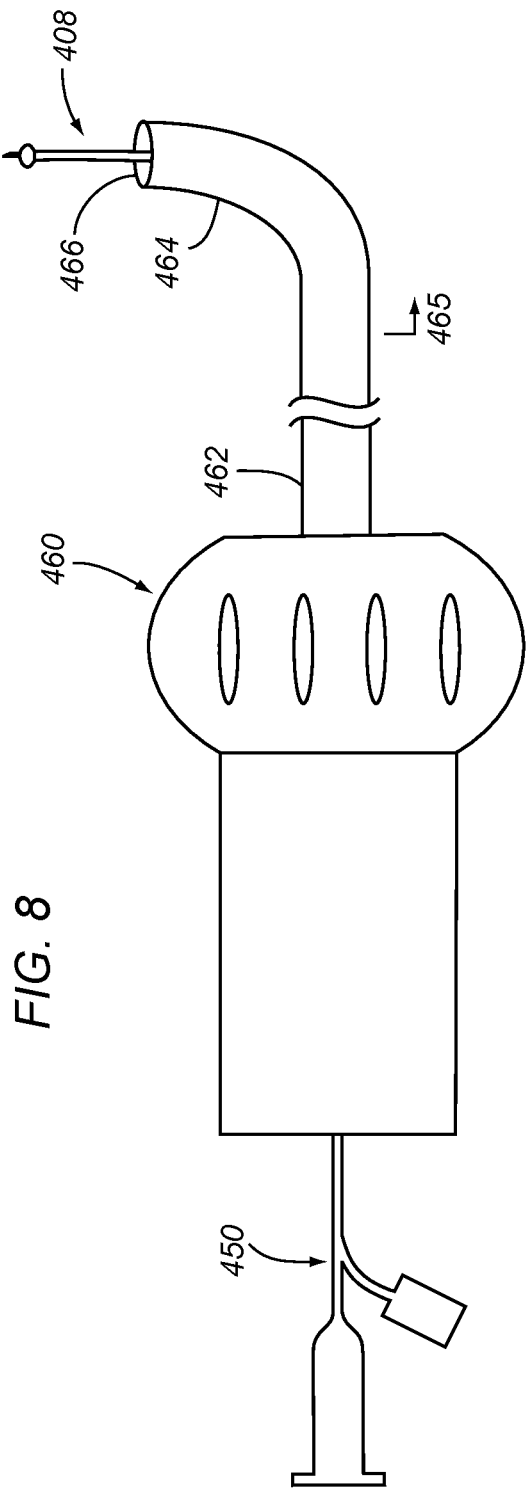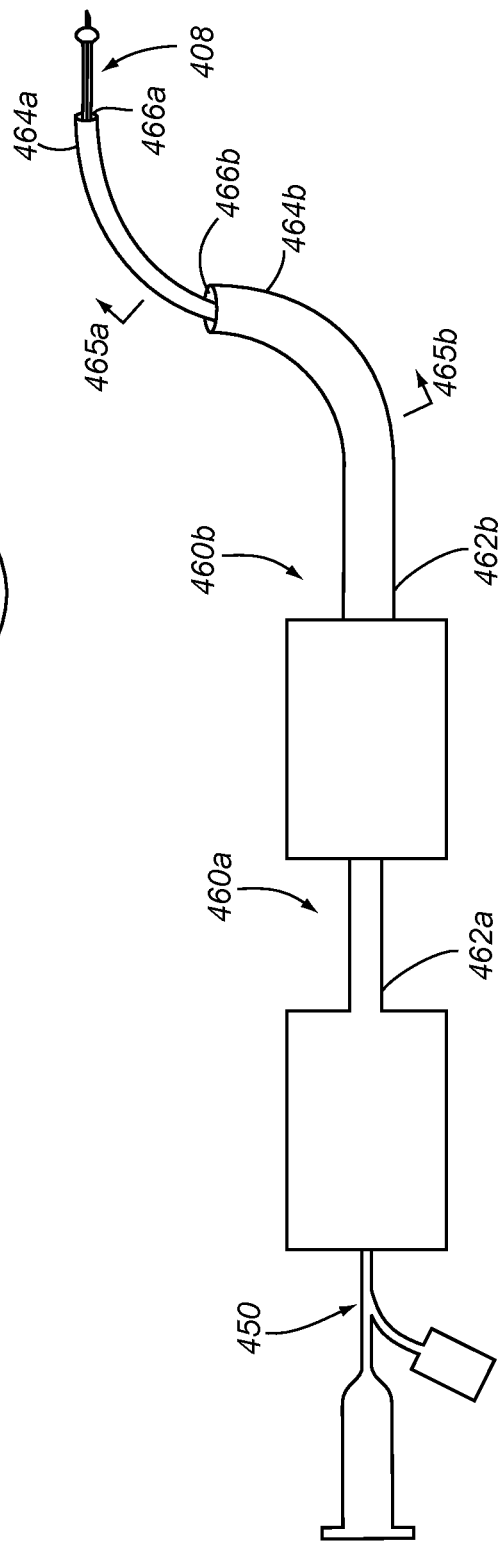

INJECTION DEVICES AND SYSTEMS AND METHODS FOR USING THEM

RELATED APPLICATION DATA

This application is a continuation of application Ser. No. 15/284,466, filed Oct. 3, 2016, issuing as U.S. Pat. No. 10,500,332, which claims benefit of provisional application Ser. Nos. 62/250,125, filed Nov. 3, 2015, and 62/299,553, filed Feb. 24, 2016, the entire disclosures of which are expressly incorporated by reference herein.

FIELD OF THE INVENTION

The present invention relates generally to apparatus, systems, and methods for performing medical procedures, and more particularly to needles or other injection devices, and to systems and methods for injecting one or more agents into tissue, e.g., into tissue of a patient's heart, using such injection devices.

BACKGROUND

While injection devices and needle systems have been in use for many years, recent developments in minimally invasive procedures require needle systems capable of accessing distant or difficult to access regions of the body, capable of delivering agents of high viscosity (e.g., chemoembolization agents, depot drug formulations, fillers, etc.), capable of delivering agents with low shear (cells), and/or capable of delivering agents at high flow rates.

Injection devices may include a simple needle attached to a syringe, a needle assembly designed to pass through the working channel of an endoscope or catheter or other minimally invasive introduction device, and/or a needle incorporated into a more complicated device. In such cases, injecting viscous fluids into a body cavity, space, or tissue involves a number of unique challenges compared to injecting non-viscous fluids. These challenges/problems include, among others, efficient movement of the fluid with minimized pressure requirement and/or shear force, clog prevention, clog elimination/clearing, multiple sequential injections, injection of one or more additional, in some cases less viscous, fluids sequentially or intermittently without significant cross contamination, etc.

Further, the need for flexible catheter-based needle injection systems has increased in recent years given the proliferation of potential injectable materials (e.g., stem cells, ablative agents, chemotherapeutic agents, bio-polymers, other pharmaceuticals, etc.). The benefits of these materials frequently depend on the ability to precisely target their delivery to specific anatomical locations, which depends on many common catheter challenges most especially flexibility. Additionally, in the case of viscous fluids or high volume injections, the need arises for a design to balance two conflicting objectives—a small needle to minimize trauma, etc. and a large diameter to enable ease of injection, e.g., to maximize or permit adequate flow at a reasonable pressure, e.g., which can be easily generated by a handheld syringe.

Thus, traditional needles and injection systems have been shown to have a number of potential drawbacks. Therefore, apparatus and methods that facilitate injection of such materials would be useful.

SUMMARY

The present invention is directed to apparatus, systems, and methods for performing minimally invasive medical procedures. More particularly, the present invention is directed to needles or other injection devices, and to systems and methods for injecting one or more agents into tissue, e.g., into tissue of a patient's heart, using such injection devices.

In accordance with one embodiment, a device is provided for injecting one or more agents into tissue within a patient's body that includes a tubular member comprising a proximal end, a distal end sized for introduction into a patient's body, and a lumen extending between the proximal and distal ends; and a tubular extension extending distally beyond the distal end to a distal tip, the tubular extension having a cross-section smaller than the distal end and a passage communicating between the lumen and an outlet in the distal tip. Optionally, the device may also include a manifold coupled to the proximal end comprising a source of injectable material and an actuator for selectively directing the injectable material from the source through the lumen and out the outlet.

In accordance with another embodiment, a system is provided for injecting one or more agents into tissue within a patient's body that includes a needle device including a tubular member comprising a proximal end, a distal end sized for introduction into a patient's body, and a lumen extending between the proximal and distal ends, and a tubular extension extending distally beyond the distal end to a distal tip, the tubular extension having a cross-section smaller than the distal end and a passage communicating between the lumen and an outlet in the distal tip. In addition, the system may include one or more introducer devices for receiving the needle device therethrough. In addition or alternatively, the system may include a manifold coupled to the proximal end comprising a source of injectable material and an actuator for selectively directing the injectable material from the source through the lumen and out the outlet.

In accordance with yet another embodiment, a device is provided for injecting one or more agents into tissue within a patient's body that includes a substantially axially incompressible elongate member comprising a proximal end, a distal end sized for introduction into a patient's body, and a lumen extending between the proximal and distal ends; a distal stop on the distal end; and a needle tip extending distally beyond the distal stop, the needle tip having a cross-section smaller than the distal end and a passage communicating between the lumen and an outlet in the distal tip, the passage having a cross-section smaller than the lumen. In an exemplary embodiment, the elongate member includes a coil extending between the proximal and distal ends, and a sleeve disposed within an interior region of the coil extending between the proximal and distal ends, the sleeve defining the lumen and free-floating within at least a portion of the coil.

In accordance with still another embodiment, a device is provided for injecting one or more agents into tissue within a patient's body that includes a substantially axially incompressible elongate coil comprising a proximal end, a distal end sized for introduction into a patient's body; a sleeve disposed within an interior region of the coil and extending between the proximal and distal ends such that the sleeve is free-floating along at least a portion of its length between the proximal and distal ends, the sleeve defining a lumen extending between the proximal and distal ends; a tensile element coupled to the proximal and distal ends of the coil; and a needle tip extending from the distal end of the coil and having a cross-section smaller than the distal end, the needle tip comprising a passage communicating between the lumen and one or more outlets in the needle tip, the passage having a cross-section smaller than the lumen.

In accordance with yet another embodiment, a device is provided for injecting one or more agents into tissue within a patient's body that includes a substantially radially fixed tubular member comprising a proximal end and a distal end sized for introduction into a patient's body, at least a distal portion of the tubular member being sufficiently flexible to allow introduction into tortuous anatomy within a patient's body; a flexible, fluid-tight member disposed within an interior region of the tubular member and extending between the proximal and distal ends, the fluid-tight member defining a lumen extending between the proximal and distal ends, the fluid-tight member being expandable within the interior of the tubular member when exposed to internal fluid pressure with the tubular member limiting expansion of the fluid-tight member; and a needle tip extending from a distal end of the tubular member and having a cross-section smaller than the distal end, the needle tip comprising a passage communicating between the lumen and one or more outlets in the needle tip, the passage having a cross-section smaller than the lumen.

In one embodiment, the tubular member may include a coil including windings extending between the proximal and distal ends and a tensile element coupled to the proximal and distal ends and, optionally, a jacket surrounding the coil. In addition or alternatively, the fluid-tight member may include a membrane or bladder.

In accordance with yet another embodiment, a method is provided for injecting one or more agents into tissue, e.g., into a patient's heart. The method includes providing an injection device comprising an elongate member including a proximal end, a distal end, and a lumen extending therebetween; a distal stop; and needle tip extending from the distal stop. The distal end of the elongate member is introduced into a body lumen adjacent a target injection site; the needle tip is inserted into tissue at the target injection site until the distal stop contact the tissue; and material is delivered from a source through the lumen and through the needle tip into the tissue.

In accordance with still another embodiment, a method is provided for delivering one or more agents into tissue that includes providing an injection device comprising an elongate member including a proximal end, a distal end, a primary lumen and a secondary lumen extending therebetween; a distal stop; and needle tip extending from the distal stop including a passage communicating with both the primary lumen and the secondary lumen; introducing the distal end of the elongate member into a body lumen adjacent a target injection site; delivering contrast through the secondary lumen and the passage into the target injection site; using external imaging to confirm that the needle tip is positioned at the target injection site; delivering material through the primary lumen and the passage into the target injection site; and delivering fluid through the secondary lumen to clear residual material from the passage.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 7 is a side view of another embodiment of a needle device.

FIG. 7A is a detail of a distal tip of the needle device of FIG. 7.

FIGS. 8 and 9 are side views of alternative embodiments of systems for delivering a needle device, such as the needle device of FIG. 7.

DETAILED DESCRIPTION OF THE EXEMPLARY EMBODIMENTS

Figure 1:
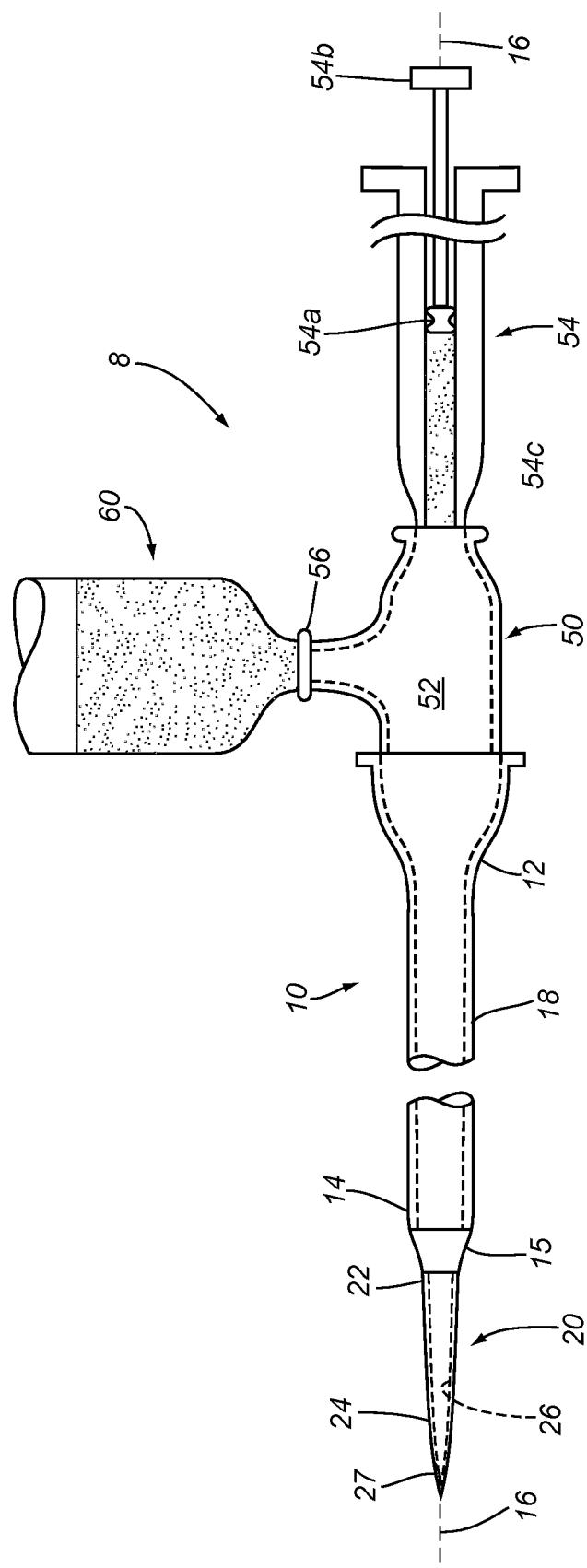
FIG. 1 is a side view of an exemplary embodiment of a needle device including a main needle body terminating in a low profile tip and a manifold including a source of injectable material.

Turning to the drawings, FIG. 1 shows an exemplary embodiment of a needle or injection device 8 for performing a medical procedure within a patient's body, e.g., for injecting one or more agents into tissue, e.g., into the wall of a patient's heart (not shown). For example, the device 8 may be used to deliver viscous fluids, gels, and/or other flowable materials, e.g., including one or more diagnostic and/or therapeutic compounds (generally referred to herein as "agents" or "materials").

As shown, the injection device 8 generally includes an elongate needle shaft or tubular member 10 including a proximal end or portion 12, a distal end or portion 14 sized for introduction into a patient's body, one or more lumens (e.g., lumen 18 shown in phantom) extending between the proximal and distal ends 12, 14, and a relatively low profile distal extension or needle tip 20. Optionally, the device 8 may include one or more features therein, e.g., adjacent the distal extension 20 to provide one or more of clog prevention, clog-clearing, and/or fluid bypass, as described elsewhere herein.

In addition, the device 8 may include a manifold or handle 50 coupled to the proximal end 12, e.g., including one or more sources of injectable material (e.g., internal chamber 58 and/or external source 60), and one or more actuators, e.g., plunger 52 for directing injectable material from the source(s) 58, 60 through the lumen 16 and out the distal extension 20. Optionally, one or more additional components or devices may be provided, e.g., an access or delivery sheath, endoscope, one or more stylets, and/or one or more guidewires or rails (not shown) to provide a system for performing a procedure, as described elsewhere herein.

Generally, the shaft 10 is an elongate tubular member defining a central longitudinal axis 16 extending between the proximal and distal ends 12, 14, and one or more lumens 18 extending between the proximal and distal ends 12, 14. In the embodiment shown in FIG. 1, the shaft 10 may include a single lumen 18 formed within the wall of the shaft 10. Alternatively, the shaft 10 may include one or more additional lumens within the wall of the shaft 10 (not shown), if desired, or the shaft 10 may be formed as one or more separate tubular members (also not shown) within an outer tubular shaft, e.g., similar to other embodiments described elsewhere herein.

Optionally, the shaft 10 may include one or more features to enhance visibility under ultrasound, Mill or other imaging modalities, e.g., by providing one or more radiopaque markers on and/or doping one or more regions adjacent the distal extension 20, e.g. as known in the art. For example, as shown in FIG. 1, a radiopaque marker 15 may be provided at a transition from the distal end 14 to the distal extension 20 to facilitate identification of the distal extension 20.

The shaft 10 may be substantially flexible, semi-rigid, and/or rigid along its length, and may be formed from a variety of materials, including plastic, metal, and/or composite materials, as is well known to those skilled in the art. In addition, the shaft 10 may have a substantially uniform outer diameter (or other cross-section) between the proximal and distal ends 12, 14, or the diameter may vary along the length of the shaft 10.

For example, in one embodiment, the shaft 10 may have a substantially uniform construction and size along its length between the proximal and distal ends 12, 14. Alternatively, a distal portion of the shaft 10, e.g., having a length of about ninety centimeters or more (90 cm), immediately adjacent to or spaced a predetermined distance from the distal extension 20, may be substantially flexible to facilitate advancement through tortuous anatomy, while a proximal region, e.g., extending a predetermined distance from the proximal end 12, e.g. about thirty centimeters (30 cm) or more, may be semi-rigid or rigid to enhance pushability and/or torqueability of the shaft 10 without substantial risk of buckling or kinking. Optionally, the lumen 18 may include lubricious material or may be formed from one or more layers of thermoplastic or other polymeric material including one or more coatings on the inner surface thereof having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

The distal extension 20 may be coupled to and/or otherwise extend distally from the distal end 14 of the shaft 12, e.g., such that the shaft 12 defines a main portion of the device 10 and the distal extension 20 defines a smaller penetrating needle portion. In one embodiment, the distal extension 20 may be a single tubular body having a first end 22 coupled to the distal end 14 of the shaft 12, and a second end 24 terminating in a tip 25 having a beveled, multi-faceted grind, trocar grind, or other sharpened shape, as desired to facilitate penetration into tissue. A passage or lumen 26 may extend from the first end 22 to one or more outlets, e.g., outlet 27, in the second end 24. In addition or alternatively, one or more outlets may be provided along the outer surface of the distal extension 20, e.g., adjacent to or instead of the outlet 27. In addition or alternatively, the distal extension 20 may be substantially straight, e.g., as shown in FIG. 1, or may be formed in a fixed curved or other curvilinear shape, e.g., to facilitate securement and/or accessing tissue not directly aligned with the longitudinal axis 16.

In an exemplary embodiment, the distal extension 20 may be formed from a section of hypotube or other uniform tubular body, similar to conventional needles e.g., formed from metal, such as stainless steel, plastic, or composite material, having desired mechanical properties, e.g., sufficient column strength to allow the distal extension 20 to be directed into tissue by manipulating the shaft 10 from the proximal end 12. In exemplary embodiments, the distal extension 20 may have a relatively thin wall, e.g., no larger than 25 gauge, or no larger than 32 gauge, to reduce the rigidity of the distal extension 64, if desired. The proximal end 22 of the distal extension 20 may be attached to the distal end 14 of the shaft 10, e.g., by one or more of interference fit, cooperating connectors, bonding with adhesive, fusing, welding, soldering, and the like, e.g., such that the distal extension 20 is centered on the distal end 14 and extends substantially parallel to the longitudinal axis 14. Alternatively, the distal extension 20 may be coupled to a separate manifold or other connector (not shown), e.g., an enlarged stop member similar to that shown in FIG. 7A and described further elsewhere herein, which may be larger than the distal end 14 of the shaft 10 to provide enhanced tactile feedback or otherwise limit penetration of the distal extension 20 into tissue.

Figure 2:
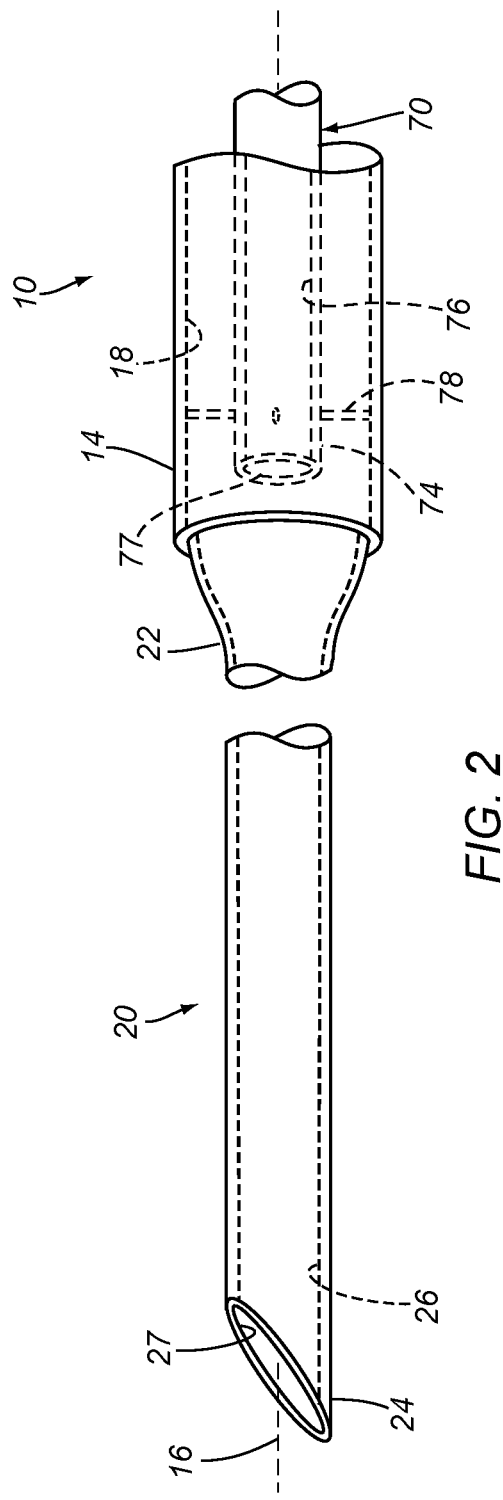
FIGS. 2 and 3 are details of alternative embodiments of needle tips that may be provided on a needle device, such as the needle device of FIG. 1, to allow different materials to be delivered quickly from the device.
Figure 3:
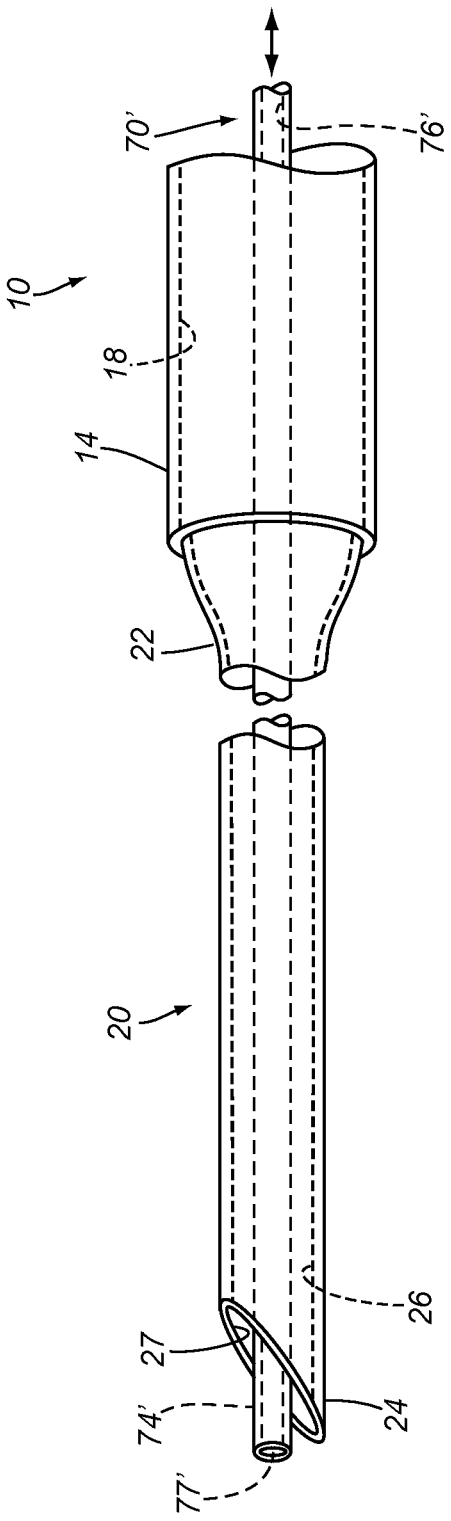

As shown in FIG. 1, a tapered or flared transition may be provided at the first end 22 of the tubular extension 20 to facilitate connection to the distal end 14 of the shaft 10. For example, as shown in FIGS. 2 and 3, the first end 22 of the tubular extension 20 may flare radially outwardly to a size such that the flared transition may be seated within the distal end 14 of the shaft 10 and then substantially permanently attached thereto, e.g., using one or more of bonding with adhesive, fusing, soldering, sonic welding, molding, and the like. Alternatively, a blunt transition (not shown) may be provided if desired, e.g., to provide a stop, which may provide tactile feedback or otherwise prevent directing the tubular extension 20 too deep into tissue. For example, the transition from the shaft 10 to the distal extension 20 may provide depth control, e.g., to limit penetration into tissue, which may be particularly useful when injecting agent(s) into some tissue structures, e.g., into the epicardium, myocardium, and the like, without penetrating entirely into or out of a chamber of the heart.

Thus, the entire shaft 10 or at least the distal end 14 of the shaft 10 may have a first outer diameter and the tubular extension 20 may have a second outer diameter that is smaller than the first outer diameter. In exemplary embodiments, the first outer diameter may be between about 0.040-0.080 inch (1.0-2.0 mm) and the second outer diameter may be between about 0.010-0.025 inch (0.025-0.0625 mm), e.g., about ten to fifty percent (10-50%) smaller than the first outer diameter. Similarly, the shaft 10 may have a first length between the first and second ends 12, 14 that is substantially longer than a second length of the distal extension 20, e.g., such that the shaft 10 may extend from an access site, e.g., a percutaneous access site in the patient's skin through the patient's vasculature to a target treatment site, e.g., a chamber within the patient's heart. In exemplary embodiments, the first length may be between about forty and one hundred forty centimeters (40-140 cm) and the second length may be between about two and fifteen millimeters (2-15 mm), e.g., not more than about five millimeters (5 mm).

Another potential advantage of having the shaft 10 larger than the distal extension 20 is that the lumen 18 of the device 8 may have a relatively larger diameter along most of the length of the device 8, e.g., along the entire length of the shaft 10 if the shaft 10 has a substantially uniform diameter between the proximal and distal ends 12, 14. For example, if a single lumen 18 is provided in the shaft 10, the inner diameter of the lumen 18 may be maximized, which may reduce friction for materials passing through the lumen 18, which may be particularly useful for viscous fluids or to reduce shear on fluids passing through the lumen 18. The passage 26 through the distal extension 20 may have a diameter substantially smaller than the lumen 18 but, given its relatively short length, may add minimal resistance to deliver such fluids. Thus, with the resistance to flow lower within the lumen 18 of the shaft 10 than within the passage 26 of the distal extension 20, the overall force needed to deliver the fluids may be reduced, as compared to a uniform diameter lumen sized similar to the passage 26.

With continued reference to FIG. 1, the manifold 50 may be provided on the proximal end 12 of the shaft 10 to contain and allow delivery of one or more injectable materials. In one embodiment, the manifold may be configured and/or sized to provide a handle for holding and/or manipulating the device 8 from the proximal end 12. Alternatively, the device 8 may include a separate handle (not shown) coupled to the proximal end 12 of the shaft 10 and the manifold may be coupled to a port of the handle that communicates with the lumen 18.

As shown, the manifold 50 includes a relatively low volume chamber 52 therein and an actuator 54 for directing fluid or other material within the chamber 52 into the lumen 18. In addition, the manifold 50 includes a port 56 communicating with the chamber 52 to which a relatively high volume source of material 60 may be coupled. For example, the port 56 and source 60 may include cooperating connectors (not shown) to allow the source 60 to be selectively coupled and/or removed from the manifold 50, as desired.

In the embodiment shown, the actuator 54 is a syringe including a piston 54a on a distal end of a plunger 54b that is slidably disposed within a passage 54c communicating with the chamber 52. Proximal movement of the plunger 54b withdraws the piston 54a within the passage 54c, thereby creating a vacuum within the chamber 52 and drawing material from the source 60 through the port 56 into the chamber 52. Distal advancement of the plunger 54b advances the piston 54a and increases pressure within the chamber 52, thereby directing material from the chamber 52 through the lumen 18. Alternatively, other actuators may be provided, if desired. For example, for viscous materials, a screw actuator (not shown) may be provided to direct the piston 54a proximally and distally, which may be provide a mechanical advantage than directly manipulating the piston 54a using the plunger 54b, or a motorized pump or other driver (not shown) may be provided.

Optionally, the port 56 may include one or more features to control or limit introduction of material from the source 60 into the chamber 52. For example, in one embodiment, a check valve, e.g., a duck valve or flap valve (not shown), may be provided that allows flow only in one direction, i.e., from the source 60 into the chamber 52. Thus, if pressure is reduced within the chamber 52, e.g., by drawing the plunger 54b proximally, the valve may open to allow material to pass through the port 56 into the chamber 52 from the source 60. Conversely, if pressure is increased within the chamber 52, e.g., by advancing the plunger 54d distally, the valve may automatically close to prevent material within the chamber 52 from returning back into the source 60 and, instead, travel into the lumen 18.

In an alternative embodiment, a manual stopcock or other switch (not shown) may be provided on the port 56, which may be selectively opened and closed. For example, the switch may be opened to allow material to pass from the source 60 through the port 56 into the chamber 52, e.g., by drawing the plunger 54b proximally, and then closed once sufficient material is introduced into the chamber 52 to isolate the chamber 52 from the source 60. Thereafter, the plunger 54b may be advanced distally to deliver the material from the chamber 52 through the lumen 18.

In an alternative embodiment, the source 60 may be substantially permanently attached, fixed, or integrated to the manifold 50. In this alternative, the source 60 may include one or more openings, e.g., ports, Luer connectors, and the like (not shown), to allow the source 60 to be refilled with material. Optionally, the source 60 may include more than one reservoir therein, which may be filled with different agents, e.g., such that the agents mix when material is drawn from the source 60 into the chamber 52. In this option, the source 60 may include one or more mixing elements (not shown) to mix the agents together as they exit the source 60, e.g., to initiate polymerization reactions, activate adhesives, and the like. Thus, materials that may react with one another may be kept separated within the source 60 for an indefinite period of time, and then mixed and drawn into the chamber 52 immediately before delivery into a patient's body, e.g., such that the materials may be delivered through the lumen 18 before the reaction is complete.

Optionally, the manifold or handle 50 may include one or more additional ports (not shown) communicating with respective lumens within the shaft 10. For example, if a bypass lumen is provided within the shaft 10, e.g., as shown in FIGS. 2 and 3, a port communicating with the bypass lumen may be provided for delivering one or more fluids through the bypass lumen, as described elsewhere herein.

Figure 4:
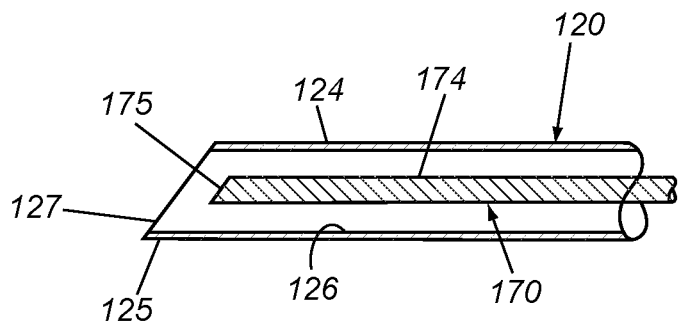
FIGS. 4-6 are details of alternative embodiments of clearing elements that may be provided within a needle device, such as the needle device of FIG. 1.
Figure 5:
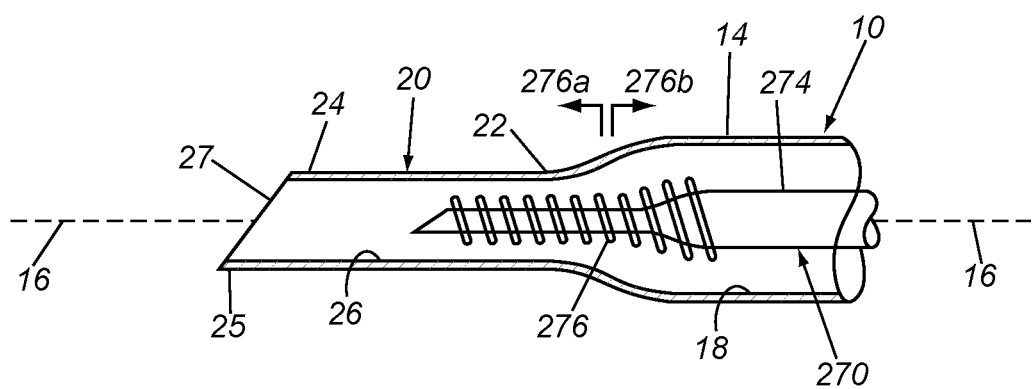
Figure 6:
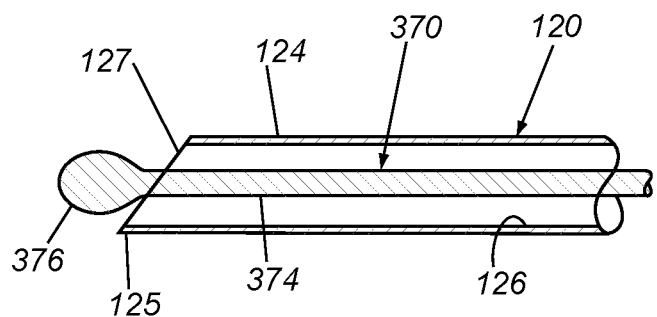

In addition or alternatively, the manifold or handle 50 may also include one or more actuators, such as sliders, buttons, switches, rotational actuators, locks, and the like, e.g., for activating and/or manipulating components on the distal end 14 or otherwise operating the device 8. For example, if an advanceable bypass lumen is provided within the shaft 10, e.g., as shown in FIG. 3, or a clearing element is provided within the shaft 10, e.g., as shown in FIGS. 4-6, an actuator (not shown) may be provided that is coupled to the element for advancing and retracting the element, rotating the element, and the like, as described further elsewhere herein.

Turning to FIG. 2, an exemplary embodiment of a bypass member 70 is shown that may be included in a needle device, such as the needle device 8 of FIG. 1. As shown, the bypass member 70 is an elongate tubular body including a proximal end (not shown), a distal end 74 disposed within the shaft 10 immediately adjacent the distal extension 20, and a bypass lumen 76 extending therebetween. As shown, the bypass member 70 may be disposed concentrically within the shaft 10, e.g., such that the distal end 74 is substantially centered along central axis 16 within the shaft lumen 18 and terminates a predetermined distance from the proximal end 22 of the distal extension 20.

Alternatively, the distal end 74 of the bypass member 70 may be coupled to a manifold or connector (not shown) attached to the distal end 14 of the shaft 10, which may include one or more passages, side holes, or other ports (also not shown), e.g., to allow fluid to pass through the bypass lumen 76 and the port(s). With the bypass member 70 coupled to the proximal and distal ends 12, 14 of the shaft 10, the bypass member 70 may act as a tensile element, e.g., to provide tensile strength and/or prevent elongation of the shaft 10 during use. For example, if the shaft 10 were constructed as a coil carrying a liner (not shown), e.g., similar to the shaft 410 shown in FIG. 7 and described elsewhere herein, the coil may provide column strength but not tensile strength. The bypass member 70 may be constructed from a braid-reinforced tubular body, e.g., polyimide and the like having a relatively high rigidity and/or high strength, having a diameter smaller than the shaft 10. Coupling the opposite ends of the bypass member 70 to the ends of the shaft 10 may provide desired tensile strength yet maintain flexibility given the relatively small diameter of the bypass member 70.

Proximal to the distal end 74, the bypass member 70 may be supported concentrically within the lumen 18, e.g., fixed at one or more locations along the length of the shaft 10, or may be at least partially free-floating such that the bypass member 70 is free to move laterally within the shaft 10, e.g., to accommodate bending of the shaft 10. Alternatively, at the distal end 74 or at one or more other locations, the bypass member 70 may be supported or attached non-concentrically, e.g., against the sidewall of the shaft 10 or simply aligned off the central axis 16. At the proximal end, the bypass member 70 may communicate with a port on a manifold or handle (not shown), e.g., such that a source of fluid, such as saline, contrast, and the like, may be coupled to the port to deliver fluid through the bypass lumen 76, as described further elsewhere herein.

The bypass member 70 has an outer diameter or other maximum cross-section that is smaller than the inner diameter of the shaft lumen 18 such that fluid may flow through the shaft lumen 18 between the shaft proximal and distal ends 12, 14 around the bypass member 70, i.e. through the annular space between the bypass member 70 and the shaft 10. Given the continuous tubular wall of the bypass member 70, materials introduced through either the shaft lumen 18 or the bypass lumen 76 may remain isolated from one another along the length of the shaft 10, e.g., until the region beyond the distal end 74 of the bypass member 70.

As shown, the distal end 74 of the bypass member 70 may be supported within the distal end 14 of the shaft 10, e.g., by one or more struts, supports, sleeves, and/or other support elements or connectors 78. In one embodiment, the distal end 74 may be attached or otherwise fixed to the support elements 78, which may also be attached or fixed relative to the shaft 10. In exemplary embodiments, the support elements 78 may be fixed to the bypass lumen 70 and/or shaft 10 by one or more of an interference fit, cooperating connectors, bonding with adhesive, sonic welding, brazing, soldering, laser or resistance welding, and the like. Thus, in this embodiment, the bypass member 70 may be axially fixed relative to the shaft 10, e.g., such that an outlet 77 of the bypass lumen 76 is disposed adjacent to the passage 26 of the distal extension 20 at a fixed spacing.

In this manner, fluid introduced through the bypass lumen 76 of the bypass member 70 may exit the outlet 77 into the shaft lumen 18 and then into the passage 26 of the distal extension 20 to exit the outlet 27. In addition, fluid or other materials may also be delivered through the shaft lumen 18 around the bypass member 70 into the passage 26 to exit the outlet 27. Thus, if it is desired to deliver a fluid through the bypass member 70 after delivering material from the shaft lumen 18, the fluid exiting the bypass outlet 77 need only clear a short volume of residual material, i.e., between the bypass outlet 77 and the outlet 27 rather than having to clear the entire shaft lumen 18 if the bypass member 70 were omitted. For example, saline and the like may be delivered through the bypass lumen 76 at any time, e.g., to flush the passage 26 if the material from the shaft lumen 18 is reacting material that may potentially clog the passage 26 if it remains and fully reacts and/or solidifies. In addition or alternatively, contrast (e.g., radiopaque, sonographically visible, visible under Mill, etc.) or other material may be delivered through the bypass lumen 76 at any time to assist in imaging and/or positioning the device 8 and/or identifying the location of the distal extension 20, as described elsewhere herein.

For example, during a procedure, a relatively small volume of contrast may be delivered via the bypass lumen 76 to confirm location (e.g., using fluoroscopy or other external imaging), and then a relatively large volume of material may be delivered via the shaft lumen 18 into tissue at the location. Thereafter, a small volume of contrast may be delivered via the bypass lumen 76 to clear the passage 26, and, if desired, the process may be repeated at one or more additional locations. Such a procedure may reduce the risk of injecting agents, such as chemo-agents, agents with embolic potential, and the like, at the wrong location where they may have undesired adverse effects.

Alternatively, as shown in FIG. 3, a bypass member 70' may be provided that is axially movable relative to the shaft 10. In this embodiment, the bypass member 70' generally includes a proximal end communicating with a port on a handle or manifold (not shown), a distal end 74' disposed within the shaft 10, and a bypass lumen 76' extending therebetween, similar to the bypass member 70 shown in FIG. 2. The bypass member 70' may be disposed concentrically within the shaft 10, e.g., such that the distal end 74' is substantially centered within the shaft lumen 18 and aligned with the passage 26 through the distal extension 20.

Optionally, the bypass member 70' may be supported concentrically within the lumen 18, e.g., by one or struts, sleeves, or other support or guide members (not shown) such that the bypass member 70' is supported laterally but is free to slide axially relative to the support member(s). For example, a guide member (not shown) may be provided within the distal end 14 of the shaft 10 to guide the distal end 74' of the guide member 70' into the passage 26. Proximal to the guide member, the bypass member 70' may be supported by one or more additional guide members or may be at least partially free-floating such that the bypass member 70' is free to move laterally within the shaft lumen 18, similar to the bypass member 70 shown in FIG. 2.

The bypass member 70' has an outer diameter or other maximum cross-section that is smaller than the inner diameter of the passage 26 of the distal extension 20 such that the distal end 74' may be introduced into the passage 26, e.g., as shown in FIG. 3. In one embodiment, the outer diameter of the bypass member 70' may be smaller than the passage 26 such that material may be delivered from the shaft lumen 18 through the passage 26 around the bypass member 70.' Alternatively, the bypass member 70' may have an outer diameter similar to the inner diameter of the passage 20 such that the bypass member 70' slidingly and/or sealingly engages the inner surface of the distal extension 20. Thus, in this alternative, the distal end 74' of the bypass member 70' may be advanced into the passage 20, e.g., to clear material within the passage 20 and/or to prevent additional material from the shaft lumen 18 entering the passage 20 and exiting the outlet 27.

Optionally, the bypass member 70' and shaft 10 may include corresponding stops (not shown) to limit axial movement of the bypass member 70' or, alternatively, such stops may be provided in the manifold or handle at the proximal end. For example, movement of the bypass member 70' may be limited between a proximal position, e.g., where the outlet 77' is positioned within the shaft lumen 18, e.g., spaced a predetermined distance proximally from the passage 20, similar to the position shown in FIG. 2, and a distal position.

In one embodiment, the distal position may result in the distal end 74' and outlet 77' being exposed from the outlet 27 of the distal extension 20, as shown in FIG. 3. In this embodiment, the distal end 74' may have a beveled, multi-faceted grind, or other sharpened tip to facilitate penetration into tissue, a bulbous, rounded, or other atraumatic tip (not shown), and the like, as desired. In an alternative embodiment, the distal position may limit the distal end 74' to remain within the distal extension 20, i.e., such that the distal end 74' is not exposed from the outlet 27.

During use, the distal end 14 of the shaft 10 may be introduced into a patient's body, with the bypass member 70' in the proximal position, and advanced to a desired location. At any time, the bypass member 70' may be advanced, e.g., into the passage 20 or from the outlet 27, and fluid may be delivered from the bypass lumen 76,' e.g., without risk of mixing or contaminating fluid within the shaft lumen 18. For example, with the distal extension 20 positioned at a target injection site (not shown), the bypass member 70' may be advanced from the outlet 27 and contrast material delivered into the site to confirm the location of the distal tip 24 of the distal extension 20, e.g., before or after inserting the distal extension 20 into tissue at the site. Once the location is confirmed and/or the distal extension 20 penetrated into tissue, the bypass member 70' may be withdrawn, and material may be delivered from the shaft lumen 18 through the passage 20 into the site, e.g., using the actuator 50 shown in FIG. 1 and using the methods described elsewhere herein. At any time, the bypass member 70' may be advanced again, thereby clearing the passage 20 or directing the distal end 74' through the passage 20, e.g., to confirm the location, verify material delivery, and/or when moving to one or more additional injection sites.

In another embodiment, a clearing element may be provided within a needle device, such as the needle device 8 of FIG. 1. There are a number of mechanisms that may lead to clogging, e.g., contamination, drying, ongoing polymerization or curing, etc. Prevention of contamination is of primary importance and may be improved using non-marring/galling materials, etc. that may shed particulate. Additionally, materials that are highly impermeable to fluid/material may prevent drying or crusting of the materials. Additionally, ongoing polymerization of a material may cause clogging. To address these potential problems, a needle clearing element may be provided that can traverse the necessary portion of the needle length to eject or otherwise "clear" whatever is blocking flow.

For example, turning to FIG. 4, an exemplary embodiment of a clearing member 170 is shown slidably disposed within a needle tip 120, e.g., a distal extension extending from a shaft, similar to the needle device 8 shown in FIG. 1. Generally, the clearing member 170 includes a proximal end (not shown) and a distal end 174 sized to be slidably received in a passage 126 through the needle tip 120. For example, the distal end 174 of the clearing member 170 may have an outer diameter similar to the inner diameter of the passage 126 such that the distal end 174 slidingly and/or sealingly engages the inner surface of the needle tip 120.

In this embodiment, the distal end 174 may be advanced into the passage 126, e.g., to clear material within the passage 126 and/or to prevent additional material from a shaft lumen (not shown) communicating with the passage 126 from entering the passage 126 and/or exiting outlet 127. The distal end 174 may include a solid tip 175 having a beveled shape corresponding a beveled tip 125 of the distal end 124 of the needle tip 120, e.g., such that the tips 125, 175 may be aligned together to provide a substantially continuous sealed tip for the needle tip 120. Alternatively, the distal end 174 of the clearing member 170 may have another shape, e.g., corresponding the shape of the distal end 124 of the needle tip 120, and/or may include a lumen (not shown), similar to the bypass members described elsewhere herein.

In this embodiment, the clearing member 170 and the needle tip 120 may include corresponding stops (not shown) to limit axial movement of the clearing member 170 (or, alternatively, such stops may be provided in the manifold or handle at the proximal end) to limit distal movement of the clearing member 170, e.g., such that the distal end 174 does not extend beyond the distal tip 125 of the needle tip 120.

Such a clearing member 170 may be configured to displace occupying fluid/material in either direction (distally or proximally), as needed, to, for example, prevent the unwanted leaking or injection of fluid/material out of the needle tip 125. The distal end 174 of the clearing member 170 may function as a plunger, pushing clogging material forward and out of the needle tip 125.

Optionally, a clearing element may be provided that includes a screw, auger, or other mechanism to draw material backward, e.g., out of a small diameter distal segment and into a larger diameter proximal segment of the needle device. In addition or alternatively, the clearing element may include a macerating element or other mechanism for breaking up or reducing the size, tenacity, etc. of any clogging material.

For example, FIG. 5 shows an exemplary embodiment of a clearing member 270 that may be provided within a needle device, e.g., within a shaft 10 and/or distal extension 20 of the needle device 8 shown in FIG. 1. Generally, the clearing member 270 includes a proximal end (not shown), a distal end 274 disposed within a distal end 14 of the shaft 10, e.g., within lumen 18, and one or more helical elements 276 providing a screw or auger. For example, a single continuous helical thread may be provided that extends along a desired length of the distal end 274 of the clearing member 270. Alternatively, multiple helical threads may be provided that are spaced apart from one another and/or the helical threads may extend discontinuously along the desired length.

At least a portion of the helical elements 276 may be sized to be received within a passage 26 of the distal extension 20, e.g., such that the helical elements 276 have a minimal clearance with the inner surface of the distal extension 20. For example, as shown, the helical elements 276 may include a first region 276a sized to be received within the passage 26 and a second region 276b proximal to the first region 276a that is larger than the passage 26. For example, in one embodiment, the first region 276a may have a substantially uniform outer diameter slightly smaller than the inner diameter of the passage 26, and the second region 276b may transition to a larger diameter, e.g., slightly smaller than the inner diameter of the lumen 18.

The clearing member 270 may be rotatable about the central axis 16 of the shaft 10, e.g., to provide a mechanism for mechanically moving material within the passage 26 proximally or distally relative to the distal extension 20. In one embodiment, the clearing member 270 may be fixed axially relative to the distal extension 20, e.g., such that the first region 276a of the helical elements 276 extends at least partially, e.g., entirely, along the length of the passage 26, and the second region 276b is located within the lumen 18.

Consequently, rotation of the clearing member 270 in a first direction may cause material surrounding the helical elements 276 to move proximally, e.g., directing material within the passage 26 back into the lumen 18. Rotation in a second direction opposite the first direction may cause material within the passage 26 (and elsewhere engaged by the helical elements 276) to move distally and exit the outlet 27. Optionally, an actuator may be provided at the proximal end, e.g., on a manifold or handle (not shown), that may be manipulated to manually rotate the clearing member 270 in either direction (or, alternatively, the actuator may only allow rotation in one direction). Alternatively, a motorized impeller may be provided that is coupled to the clearing member 270 for selectively rotating the clearing member 270 in one or both directions.

Optionally, the clearing member 270 may also be movable axially, e.g., to allow the helical elements 276 to be advanced into the passage 26 and withdrawn into the lumen 18, as desired. For example, during use, the clearing member 270 may be provided initially in a proximal position, e.g., with the helical elements 276 entirely within the lumen 18 (not shown). The shaft 10 may be introduced into a patient's body and advanced to a target injection site, where the distal extension 20 may be inserted into tissue (not shown), and material may be delivered through the lumen 18 and passage 26 into the tissue, similar to other embodiments herein.

At any time, the clearing member 270 may be advanced to insert the helical elements 276 into the passage 26 and the clearing member 270 may be rotated, e.g., to advance remaining material within the passage 26 out of the outlet 27, e.g., into tissue, or retract remaining material back into the lumen 18. Thereafter, the clearing member 270 may be withdrawn and, if desired, the shaft 10 may be introduced into another injection site where the process may be repeated. Optionally, the clearing member 270 may include one or more macerating elements, e.g., teeth or other features (not shown) on or adjacent the helical elements 276, which may be used to break up material being removed by the clearing member 270.

Turning to FIG. 6, in another embodiment, a blocker wire 370 may be provided in a needle device, such as the needle device 8 of FIG. 1. The blocker wire 370 may include a proximal end, e.g., coupled to an actuator on a manifold or handle (not shown), and a distal end 374 including a bulbous or other enlarged atraumatic tip 376. The blocker wire 370 may have sufficient length such that the tip 376 thereof may extend a short distance beyond a distal tip 125 of a needle tip 120, as shown. The blocker wire 370 may be movable between a distal position, where the tip 376 is spaced distally from the distal tip 125 of the needle tip 120, and a proximal position, where the tip 376 is withdrawn into the passage 126. Alternatively, the tip 376 have an outer diameter or other cross-section larger than the inner diameter of the passage 126 and/or larger than the outer diameter of the distal tip 120, if desired.

In this manner, the blocker wire 370 may provide a substantially atraumatic guide to facilitate advancing the needle device, e.g., through a delivery sheath, endoscope, or directly through a body lumen within a patient's body (not shown). Once the needle device is positioned at a desired location, the blocker wire 370 may be withdrawn to direct the tip 376 into the passage 20, e.g., into a larger lumen (not shown) proximal to the needle tip 120, similar to other embodiments herein, or entirely out of the needle device. Material may then be delivered through the passage 20, e.g., similar to other embodiments herein.

For example, when dealing with viscous or other fluids, it may be desirable to utilize multiple needles assemblies, e.g., as an alternative to avoid clogging, where material has a short pot life or rapid cure time, where multiple needle configurations (e.g., length, diameter, etc.) are desired, and the like. In the case where the needle device is utilized in conjunction with another device, e.g., introduced through a working channel of an endoscope or catheter, it may be desirable to introduce, remove, and/or re-introduce the needle device without risk of damaging the working channel and/or needle. In such a case, it may be desirable to avoid or minimize contact of the needle tip/bevel with the working channel. For example, the atraumatic tip 376 shown in FIG. 6 may extend through the needle tip 120 and out of the outlet 127 during introduction, removal, and/or reintroduction to prevent contact between the needle tip 120 and the channel wall, which may otherwise risk damaging the needle tip 120 or endoscope, or may even remove wall material and expose it within a patient's body. When not extended for introduction, the tip 376 may also be used to clear clogs and/or otherwise remove material from the passage 126, similar to other embodiments herein.

Turning to FIG. 7, another embodiment of a needle device 408 is shown that includes a shaft 410 including a proximal end 412 coupled to a handle or hub 450 and a distal end 414 sized for introduction into a patient's body, thereby defining a longitudinal axis 416 therebetween, and one or more lumens 418 extending between the proximal and distal ends 412, 414, generally similar to other embodiments herein. In addition, the device 408 includes an enlarged tissue stop 430 on the distal end 414 and a needle tip 420 extending from the tissue stop 430, e.g., generally aligned along the axis 416.

The shaft 410 includes a tightly wound coil 411 including one or more wire or filar elements extending helically at least partially between the proximal and distal ends 412, 414. Alternatively, the shaft 410 may have other constructions, e.g., a braided shaft, a laser-cut tube, and the like (not shown) that provide desired hoop strength and flexibility. For example, the coil 411 (or other constructions) may have sufficient hoop strength to render the shaft 410 substantially radially fixed, i.e., such that the shaft 410 is substantially unexpandable when subjected to radially outward forces, e.g., from an expandable membrane, bladder, or other sleeve disposed within the shaft 410, as described elsewhere herein. The wire element(s) may be formed from metal, plastic, or composite material having a round cross-section, although alternatively, the wire element(s) may have a square, rectangular, oval, or other cross-section, which, in some cases may provide greater compression strength and/or lower overall profile than a round cross-section. The coil 411 may be biased such that adjacent turns contact one another, e.g., to provide a lowest potential energy state, yet may provide flexibility, i.e., allowing the shaft 410 to bend, e.g., causing adjacent turns of the coil 411 to separate along the outside of a bend and remain contacting one another along the inside of a bend. Thus, the coil 411 may be biased to a substantially linear orientation, although, alternatively, the coil 411 may be biased to curvilinear shapes along one or more regions of its length, if desired, which may introduce some spaces between adjacent turns on the outside of any bends in the curvilinear shape.

Optionally, as shown in FIG. 7A, the shaft 410 may include an elongate member or tensile element 413, e.g., extending axially along the shaft 410 and coupled to one or more locations, e.g., at the distal end 414 or needle stop 430 and at the proximal end 412 (not shown). The tensile element 413 may be constructed from a solid or hollow wire, fiber, e.g., Kevlar, a braid-reinforced tubular body, a bypass member (e.g., as described elsewhere herein), and the like having a relatively high rigidity and/or high strength, and having a diameter smaller than the coil 411. Opposite ends of the tensile element 413 may be coupled to the coil 411, e.g., at the ends 412, 414 of the shaft 410, to provide desired tensile strength and/or prevent elongation of the shaft 410, yet maintain flexibility given the relatively small diameter of the tensile element 413 relative to the coil 411.

Figure 7B:
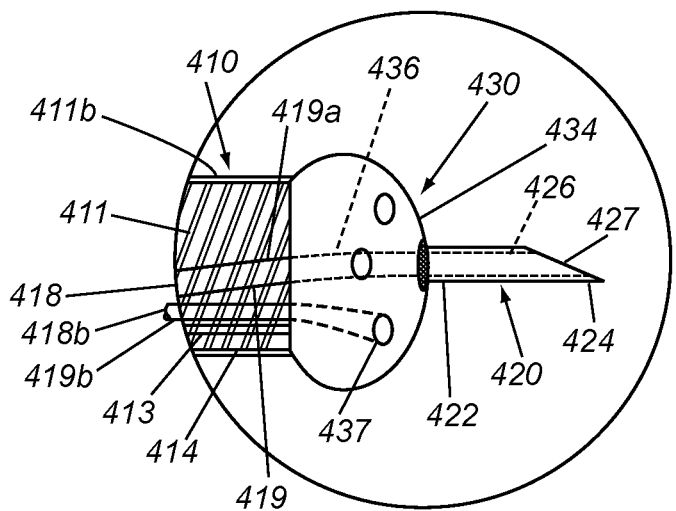
FIGS. 7B and 7C are details of alternatives of distal tips that may be provided on a needle device.

In addition or alternatively, a liner and/or jacket (not shown) may be provided on or around the coil 411. For example, as shown in FIG. 7B, a relatively thin layer 411*b* of jacket material may be dipped or otherwise applied around the outside of the coil 411 or a tubular body may be secured around the coil 411, e.g., to prevent the coil 411 from kinking and/or provide some tensile strength.

In one embodiment, the coil 411 may extend entirely from the handle 450 to the needle stop 430, thereby providing a shaft 410 that may provide a high column strength, e.g., effectively a zero compression length between the proximal and distal ends 412, 414. Thus, a distal, axial force applied to the proximal end 412, e.g., from the handle 450, may translate substantially to the distal end 414, and consequently to the needle tip 420, which may facilitate predictably penetrating the needle tip 420 into tissue at a target site within the patient's body (not shown).

Alternatively, the coil 411 may extend proximally from the needle stop 430 only partially towards the proximal end 412, e.g., to define a distal region having desired flexibility and high column strength terminating at an intermediate or proximal region, beyond which a conventional tubular catheter structure may be provided (not shown). For example, the shaft 410 may include a proximal portion constructed from a substantially rigid or semi-rigid tubular member, e.g., a section of hypotube, to enhance pushability of the shaft 410. Thus, in this alternative, the coil 411, tensile element 413, and/or other components may extend distally from the proximal portion to the needle stop 430.

To provide the lumen(s), the shaft 410 may include one or more tubular sleeves extending along the length of the coil 411, e.g., from the handle 450 to the needle stop 430 and/or along the entire length of the coil 411. For example, as best seen in FIG. 7A, a primary sleeve 419 may be provided within the interior of the coil 411 that communicates between a first port 456a on the handle 450 (shown in FIG. 7) and a passage 426 through the needle tip 420. The primary sleeve 419 may include a distal end 419a coupled to the needle stop 430 and/or the coil 411 at the distal end 414, e.g., such that the distal end 419a is substantially fixed relative to the needle stop 430 and needle tip 420 and provides a fluid-tight connection between the lumen 418 and passage 426, e.g., via one or more internal passages within the tissue stop, e.g., internal passage 436.

In one embodiment, the sleeve 419 may be a relatively thin-walled tubular body, e.g., having a wall thickness between about 0.00025-0.003 inch (0.00625-0.075 mm) or between about 0.0004-0.0005 inch (0.01-0.0125 mm), having an outer diameter that is the same as or slightly larger than the inner diameter of the coil 411. When pressurized due to fluid therein, the sleeve 419 may expand but be limited by the coil 411, which prevents further expansion, thereby allowing the sleeve 419 to carry greater pressure than it otherwise could without the coil 411. Due to the relatively thin wall of the sleeve 419, the sleeve 419 may not impact the flexibility of the coil 411, simply conforming to the shape of the coil 411. Alternatively, the sleeve 419 may have an outer diameter or other cross-section that is smaller than the inner diameter or cross-section of the coil 411. Consequently, proximal to the point of attachment, the sleeve 419 may be free-floating within the coil 411 at least partially from the distal end 414 towards the proximal end 412. Thus, when the coil 411 bends, e.g., during introduction into a patient's body, the sleeve 419 may not substantially impact the flexibility of the coil 411. Instead, the sleeve 419 may simply move towards the outside of a bend in the coil 411 and/or adopt a more curved shape within the lumen 418 to accommodate the bend.

Optionally, the sleeve 419 may be coupled to the coil 411 at one or more locations along the length of the coil 411. In one embodiment, the sleeve 419 may be coupled only at or adjacent the proximal and distal ends 412, 414, although alternatively, the sleeve 419 may be coupled to the coil 411 at one or more intermediate locations, e.g., at location 419c shown in FIG. 7.

The sleeve 419 may be formed from flexible material, e.g., plastic or composite material, e.g., PET, HDPE, nylon, PTFE, urethane, silicone, rubber, and the like, that is fluid-tight and conforms easily to the shape of the coil 411, e.g., during bending, with the tensile element 413 constraining the coil 411 longitudinally. Alternatively, the sleeve 419 may be substantially inelastic and/or has high tensile strength, e.g., such that the sleeve 419 maintains a substantially uniform inner diameter or cross-section whether empty or filled with material being delivered through the lumen 418 therein. In another alternative embodiment, the sleeve 419 may be biased to a flat or other collapsed shape that may be expanded, e.g., into a substantially uniform circular shape, when material is delivered through the lumen 418. For example, if a viscous material is delivered through the lumen 418 under high pressure, the sleeve 419 may expand with little resistance to accommodate the material within the lumen 418 and maintain a substantially uniform diameter (without further expansion under the pressures involved) to facilitate flow of the material through the lumen 418.

Alternatively, the sleeve 419 may have an outer diameter or other cross-section similar to the inner diameter or cross-section of the coil 411. Thus, in this alternative, the sleeve 419 may be attached to the coil 411 at one or more locations, e.g., only at the proximal and distal ends 419a, or substantially continuously along the length of the sleeve 419, e.g., by one or more of bonding with adhesive, fusing, and the like. In a further alternative, a sleeve may be provided outside of the coil 411, e.g., fitted closely around the coil 411 (not shown), to provide a fluid-tight wall that accommodates fluid flow through the coil 411. In this alternative, the sleeve may be secured around the coil 411 by one or more of interference fit, bonding with adhesive, fusing, and the like, e.g., at one or more locations and/or continuously along the length of the sleeve 419.

In this manner, the shaft 410 may provide a relatively large primary lumen for directing material over most of the length of the device 408, yet which communicates with a relatively small needle passage 426, similar to other embodiments herein. Although the passage 426 may have a diameter substantially smaller than the lumen 418, given its relatively short length, the passage 426 may add minimal resistance to deliver such viscous fluids. Thus, with the resistance to flow lower within the lumen 418 of the shaft 410 than within the passage 426 of the needle tip 420, the overall force needed to deliver the fluids may be reduced, as compared to a uniform diameter lumen sized similar to the passage 426.

Optionally, one or more additional sleeves and/or lumens may be provided within the shaft 410. For example, as shown in FIG. 7B, a secondary sleeve 419b may be provided within the coil 411 adjacent the primary sleeve 419, which may include a secondary sleeve lumen 418b that communicates between a second port 456b on the handle or manifold 450 and one or more infusion ports, e.g., infusion ports 437 in the tissue stop 430, as shown in FIG. 7A. The tissue stop 430 may include one or more internal passages (not shown) that communicate between a distal end of the secondary sleeve and the infusion ports 437.

During use, the primary lumen 418 may be used to introduce one or more agents, e.g., a viscous material, while the secondary lumen (which may have a smaller cross-section than the primary lumen 418) may be used to introduce relatively low viscosity materials, such as saline or contrast. For example, infusion through the secondary lumen may be used to 1) identify morphological features before placement of the needle tip 420 into tissue (e.g., using one or more radiopaque contrast agents or other imaging materials), 2) verify the needle tip 420 is fully seated in the tissue, and/or 3) verify an angle of the needle tip 420 relative to a tissue face before or after injection.

Figure 7C:
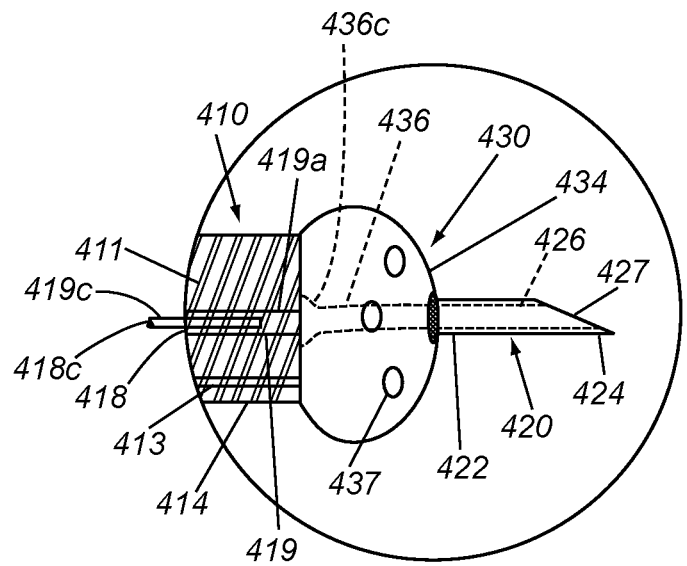

In an alternative embodiment, as shown in FIG. 7C, a secondary sleeve 419c may be provided that is located inside the primary sleeve 419, e.g., concentrically within the sleeve 419 similar to the bypass members shown in FIGS. 2 and 3. In this alternative, the tissue stop 430 may include one or more internal passages to separate the materials exiting each of the sleeves to the respective outlets 427, 437.

In a further alternative, as shown in FIG. 7C, a chamber 436c may be provided within the tissue stop 430 that communicates with the passage 426 in the needle tip 420, e.g., such that outlets of the primary sleeve 419 and the secondary sleeve 419c exit into the chamber 436c. Thus, in this alternative, material delivered from the lumen 418 of the primary sleeve 419 must pass through the chamber 436c before entering the passage 426 and exiting the outlet 427 of the needle tip 420. Similarly, material delivered from the secondary lumen must also pass through the chamber 436c before entering the passage 426 and exiting the outlet 427. Consequently, a user may alternate delivering materials from either lumen 418, 418c, with the material displacing any residual material from the other lumen only within the chamber 436c and the passage 426, e.g., similar to the bypass member 70 shown in FIG. 2 and described elsewhere herein.

With further reference to FIG. 7A, the tissue stop 430 may be a bulbous, rounded, and/or other atraumatically shaped element coupled to the distal end 414 of the shaft 410. For example, the tissue stop 430 may be attached to the coil 411 by one or more of interference fit (e.g., within the end of the coil 411 engaging around an abutment, not shown, on the tissue stop 430), bonding with adhesive, fusing, molding (e.g., with the tissue stop 430 molded into the distal end 414), welding, and the like. The tissue stop 430 may include a rounded or substantially flat distal surface 434 that is substantially larger in surface area than the cross-section of the needle tip 420, e.g., to provide tactile feedback when the needle tip 420 is inserted into tissue and/or limit insertion of the needle tip 420 into tissue.

Optionally, the needle stop 430 may have one or more flow passages that extend entirely through the needle stop 430, e.g., from a proximal location adjacent the distal end 414 of the shaft 410 to the distal surface 434. For example, the needle stop 430 may have an outer diameter larger than the distal end 414 of the shaft 410 that is intended to be slidably received within a working channel of an endoscope or catheter (not shown). Thus, when the shaft 410 and needle stop 430 are disposed within the working channel, fluid may be delivered or aspirated through the working channel, using the one or more flow passages to bypass the needle stop 430, i.e., without requiring the needle stop 430 to be deployed from the working channel. In this manner, the size of the needle stop 430 may be maximized relative to such a working channel to provide a larger stop for the needle tip 420 while still allowing fluid to pass through the working channel.

Returning to FIG. 7A, the needle tip 420 may include a proximal end 422 coupled to the tissue stop 430 and a distal tip 424, e.g., having a beveled, multi-faceted grind, or other sharpened shape to facilitate penetration into tissue, e.g., similar to other embodiments herein. For example, the needle tip 420 may be formed metal, e.g., stainless steel, Nitinol, and the like, or plastic, e.g., PET polycarbonate, and/or other high strength materials. In some embodiments, Nitinol may be desirable both for its ability to be shaped as well as its superelasticity and/or because Nitinol is softer than materials like stainless steel for the same cross-sectional profile. The proximal end 424 of the needle tip 420 may be molded into and/or otherwise attached to the tissue stop 420, similar to other embodiments herein.

Although the needle tip 420 shown in FIG. 7A is substantially straight, it will be appreciated that a curved or otherwise non-linear needle tip (not shown) may be provided, if desired. For example, a non-linear needle tip may be useful to access otherwise difficult points within tissue, e.g., to perform an endocardial injection, inject tissue near the surface of the heart at the septum (atrial or ventricular), or to distribute an infusate over a longer length than is possible compared to a straight needle.

Optionally, a balloon or other expandable member (not shown) may be provided on the distal end 414 of the shaft 410, e.g., mounted around the distal stop 430 or in place of the distal stop 430. The needle tip 420 may extend from a distal surface of the balloon, e.g., such that the balloon may be expanded to provide an enlarged contact surface and/or decrease the risk of tissue damage from inserting the needle tip 420 too far. In this embodiment, an infusion sleeve and/or lumen may be provided within the shaft 410, e.g., adjacent to or within the primary sleeve 419, as described previously.

Turning to FIGS. 8 and 9, optionally, a needle device, such as the device 408 of FIG. 7, may be coupled with other external telescoping and directional elements (e.g., independently deflectable or pre-shaped) to provide a complex range of access points and/or access angles to the tissue. For example, an ideal injection may not depend solely on the point of injections, but the entry angle or where the needle ultimately ends up within the tissue.

For example, in FIG. 8, an exemplary embodiment of a delivery sheath 460 is shown that includes a proximal end 462, e.g., coupled to a handle or hub 468, a distal end 464, and a lumen 466 extending therebetween, e.g., sized to receive the distal stop 430 and shaft 410 of the device 408 shown in FIG. 7. A distal portion 465 of the sheath 460 may be biased to a predetermined shape, e.g., a curvilinear shape, e.g., to facilitate deployment of the needle tip 420 in a desired orientation. For example, the sheath 460 may be introduced into a patient's body, e.g., from a percutaneous access site through the patient's vasculature into the patient's heart. The distal end 464 may be positioned adjacent to a target injection site, e.g., the myocardium adjacent a chamber of the patient's heart, whereupon a needle device, such as device 408, may be introduced through the lumen 466 and positioned adjacent the target site.

Optionally, contrast may be introduced into the target site, e.g., via the infusion ports 437 of the device 408 shown in FIG. 7A to confirm the location and/or orientation of the needle tip 420, e.g., before advancing the device 408 to penetrate the needle tip 420 into tissue at the target site. One or more materials may then be injected into the tissue, e.g., via the lumen 418 and passage 426 of the device 408 shown in FIGS. 7 and 7A. Optionally, the needle tip 420 may be withdrawn and the sheath 460 and device 408 repositioned to another target site, where the process may be repeated. Once sufficient material has been delivered, the needle device 408 and sheath 460 may be removed from the patient's body, e.g., using known methods.

Similarly, FIG. 9 shows a pair of telescoping pair of delivery sheaths 460a, 460b that include proximal ends 462a, 462b, distal ends 464a, 464b, and respective lumens 466a, 466b extending therebetween. As shown, each sheath 460a, 460b includes a distal portion 465a, 465b biased to a predetermined, e.g., curved, shape, yet deflectable to accommodate introduction into a patient's body, e.g., through the patient's vasculature into a chamber of the patient's heart. The distal end 464a of the first or inner sheath 460a may be sized for introduction into the lumen 466b of the second or outer sheath 460b, while the lumen 466a of the inner sheath 460a may be sized to receive a needle device, e.g., the needle device 408 of FIG. 7.

During use, the sheaths 460a, 460b may be introduced into a patient's body, e.g., into a chamber of the patient's heart (not shown), and positioned as desired. For example, the distal portion 460b of the outer sheath 460b may be positioned in a desired orientation, e.g., by rotating and/or axially manipulated to orient the distal end 464b as desired relative to a target injection site. The inner sheath 460a may then be advanced to direct the distal end 464a thereof from the distal end 464b of the outer sheath 460b and manipulated to further orient the distal end 464a relative to the target site. Optionally, both sheaths 460a, 460b may be manipulated, as desired until the distal end 464a of the inner sheath 460a is oriented as desired, whereupon a needle device 408 may be advanced from the inner sheath 460a, e.g., into tissue at the target site and deliver material from the device 408, similar to other embodiments and methods described elsewhere herein.

Although particularly useful for performing injections within a chamber of a heart, the needle devices and systems described herein may be used to perform other procedures, e.g., elsewhere within a patient's cardiovascular system or other locations within a patient's body, such as the lungs, liver, gastrointestinal tract, etc.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for injecting one or more agents into tissue within a patient's body, comprising:
    a substantially radially fixed and substantially axially incompressible tubular member comprising a proximal end and a distal end sized for introduction into a patient's body, at least a distal portion of the tubular member being sufficiently flexible to allow introduction into tortuous anatomy within the patient's body;
    a flexible, fluid-tight bladder disposed within an interior region of the tubular member and extending between the proximal and distal ends, the bladder including a distal end attached to the distal end of the tubular member, the bladder defining a lumen extending between the proximal and distal ends of the tubular member, the bladder being expandable within the interior of the tubular member when exposed to internal fluid pressure with the tubular member limiting expansion of the bladder; and
    a needle tip extending from the distal end of the tubular member and having a cross-section smaller than the distal end, the needle tip comprising a passage communicating between the lumen and one or more outlets in the needle tip, the passage having a cross-section smaller than the lumen.

2. The device of claim 1, wherein the tubular member comprises a coil including windings extending between the proximal and distal ends and a tensile element coupled to the proximal and distal ends.

3. The device of claim 2, further comprising a jacket surrounding the coil.

4. The device of claim 1, wherein the bladder is biased to a flat or other collapsed shape that is expanded when material is delivered through the lumen.

5. The device of claim 1, wherein the bladder is free-floating within the tubular member at least partially from the distal end towards the proximal end.

6. The device of claim 1, further comprising a distal stop on the distal end having an outer dimension larger than an outer dimension of the distal end of the tubular member and wherein the needle tip extends distally from the distal stop.

7. The device of claim 6, wherein the distal stop comprises a rounded or flat distal surface adjacent the needle tip to limit penetration of the needle tip into tissue.

8. A device for injecting one or more agents into tissue within a patient's body, comprising:
    a substantially axially incompressible elongate member comprising a proximal end, a distal end sized for introduction into a patient's body, and a lumen extending between the proximal and distal ends;
    a distal stop on the distal end; and
    a needle tip extending distally beyond the distal stop, the needle tip having a cross-section smaller than the distal end and a passage communicating between the lumen and an outlet in the needle tip, the passage having a cross-section smaller than the lumen,
    wherein the elongate member comprises:
    an elongate coil extending between the proximal and distal ends;
    a tensile element coupled to opposite ends of the coil; and
    a sleeve disposed within an interior region of the coil extending between the proximal and distal ends, the sleeve defining the lumen, the sleeve including a distal end attached to one of the distal stop and a distal end of the coil to provide a fluid-tight connection between the lumen and the passage and wherein at least a portion of the sleeve is free-floating within the interior region of the coil.

9. The device of claim 8, further comprising a hub on the proximal end comprising a port communicating with the lumen, thereby providing a fluid-tight path from the port to the outlet in the needle tip.

10. The device of claim 8, wherein the sleeve includes a proximal end, the device further comprising a hub on the proximal end comprising a port coupled to the sleeve proximal end, thereby providing a fluid-tight path from the port through the lumen and passage to the outlet in the needle tip.

11. The device of claim 8, wherein the sleeve is coupled to the coil only at proximal and distal ends of the coil and is free-floating within the interior region between the coil proximal and distal ends.

12. The device of claim 8, wherein the sleeve has an outer diameter smaller than an inner diameter of the coil such that the sleeve is free to move laterally within the interior region of the coil where the sleeve is free-floating within the interior region.

13. The device of claim 8, wherein the coil defines helical turns extending between the proximal and distal ends, adjacent helical turns disposed adjacent one another such that the coil has a substantially zero compression length.

14. A device for injecting one or more agents into tissue within a patient's body, comprising:
   a substantially axially incompressible elongate member comprising a proximal end, a distal end sized for introduction into a patient's body, and a lumen extending between the proximal and distal ends;
   a distal stop on the distal end; and
   a needle tip extending distally beyond the distal stop, the needle tip having a cross-section smaller than the distal end and a passage communicating between the lumen and an outlet in the needle tip, the passage having a cross-section smaller than the lumen,
   wherein the elongate member comprises:
   an elongate coil extending between the proximal and distal ends;
   a tensile element coupled to opposite ends of the coil;
   a primary sleeve disposed within an interior region of the coil extending between the proximal and distal ends, the primary sleeve defining the lumen; and
   a secondary sleeve disposed within the interior region of the coil extending between the proximal and distal ends, the secondary sleeve defining a secondary sleeve lumen extending between the proximal and distal ends that is smaller than the primary sleeve lumen.

15. The device of claim 14, wherein the secondary sleeve is disposed adjacent the primary sleeve within the interior region such that the primary and secondary sleeves are free-floating within the interior region along at least a portion of the coil between the proximal and distal ends.

16. The device of claim 15, wherein the primary and secondary sleeves are coupled to the coil only at the proximal and distal ends.

17. The device of claim 14, wherein the distal stop includes one or more infusion ports that communicate with the secondary sleeve lumen to deliver fluid through the secondary sleeve to exit through the one or more infusion ports.

18. The device of claim 14, wherein the secondary sleeve is disposed within the primary sleeve between the proximal and distal ends.

19. The device of claim 18, wherein the distal stop includes one or more infusion ports and internal passages that communicate with the secondary sleeve lumen to deliver fluid through the secondary sleeve to exit through the one or more infusion ports.

20. The device of claim 18, wherein the distal stop includes a chamber therein disposed proximal to the passage in the needle tip, and wherein the primary and secondary sleeves comprise respective outlets that communicate with the passage such that material delivered through either of the primary sleeve lumen or the secondary sleeve lumen exit the respective outlet into the chamber and pass through the passage to exit the needle tip outlet.

* * * * *